United States Patent
Jung et al.

(10) Patent No.: US 10,459,348 B2
(45) Date of Patent: Oct. 29, 2019

(54) SYSTEM AND METHOD OF INSPECTING DEVICE UNDER TEST, AND METHOD OF MANUFACTURING SEMICONDUCTOR DEVICE

(71) Applicant: SAMSUNG ELECTRONICS CO., LTD., Suwon-si (KR)

(72) Inventors: Myung-Ho Jung, Suwon-si (KR); Ji-Hoon Kang, Seongnam-si (KR); Sean Park, Yongin-si (KR); Sung-Won Park, Yongin-si (KR); Jae-Min Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 16/053,192

(22) Filed: Aug. 2, 2018

(65) Prior Publication Data
US 2019/0137884 A1    May 9, 2019

(30) Foreign Application Priority Data
Nov. 6, 2017    (KR) .................. 10-2017-0146991

(51) Int. Cl.
H04N 7/18       (2006.01)
G01N 21/95      (2006.01)
G03F 7/20       (2006.01)

(52) U.S. Cl.
CPC ........ *G03F 7/7065* (2013.01); *G01N 21/9501* (2013.01); *G06T 2207/30148* (2013.01)

(58) Field of Classification Search
CPC .... H04N 7/18; G01N 21/956; G01N 21/9501; G01N 21/95684; G01N 21/88; G06T 2207/30148; G06T 7/0004; G06T 7/001; G03F 7/7065

USPC ........ 348/126, 125, 129, 130, 133; 382/141, 382/145, 147, 149, 152
See application file for complete search history.

(56) References Cited

U.S. PATENT DOCUMENTS

| | | |
|---|---|---|
| 7,024,339 B1 | 4/2006 | Bhaskar et al. |
| 7,149,642 B1 | 12/2006 | Bhaskar et al. |
| 7,251,586 B2 | 7/2007 | Bhaskar et al. |

(Continued)

FOREIGN PATENT DOCUMENTS

| | | |
|---|---|---|
| KR | 10-2013-0085251 A | 7/2013 |
| KR | 10-1501762 B1 | 3/2015 |
| KR | 10-1635461 B1 | 7/2016 |

*Primary Examiner* — Sherrie Hsia
(74) *Attorney, Agent, or Firm* — Sughrue Mion, PLLC

(57) ABSTRACT

Inspection system for a device under test (DUT) includes an image sensor, N image obtaining devices, K switches, M image processing devices, and at least one added image processing device. The image obtaining devices are connected to the image sensor, and each of the N image obtaining devices receives image data of the image of the DUT captured by the image sensor. Each of the K switches is connected to a respective one of the image obtaining devices. Each of the M image processing devices is connected to a respective one of the switches, receives the image data that is output from one of the N image obtaining devices and is distributed by one of the K switches, and generates processed image data in real-time. The added image processing device is connected to one of the switches, receives the image data, and generates additional processed image data in real-time.

20 Claims, 8 Drawing Sheets

(56) References Cited

U.S. PATENT DOCUMENTS

| | | |
|---|---|---|
| 7,379,838 B2 | 5/2008 | Bhaskar et al. |
| 7,555,409 B1 | 6/2009 | Bhaskar et al. |
| 8,443,118 B2 | 5/2013 | Go et al. |
| 8,823,969 B1 | 9/2014 | Dubiner et al. |
| 9,386,211 B2 | 7/2016 | Soenksen |
| 9,635,340 B2 | 4/2017 | Choi |
| 2015/0177160 A1 | 6/2015 | Zoeller, III |
| 2017/0199154 A1* | 7/2017 | Nakamura ............ G01N 27/72 |
| 2018/0033704 A1* | 2/2018 | Suzuki ................. G06T 7/0008 |

* cited by examiner

SYSTEM AND METHOD OF INSPECTING DEVICE UNDER TEST, AND METHOD OF MANUFACTURING SEMICONDUCTOR DEVICE

CROSS-REFERENCE TO RELATED APPLICATION

This application claims priority under 35 U.S.C. § 119 to Korean Patent Application No. 10-2017-0146991, filed on Nov. 6, 2017 in the Korean Intellectual Property Office (KIPO), the contents of which are herein incorporated by reference in their entirety.

BACKGROUND

1. Field

This disclosure relates generally to inspection systems and methods, and more particularly to systems and methods of inspecting devices under test (DUTs), e.g., semiconductor substrates and/or display panels that are used for manufacturing semiconductor devices and/or display apparatuses, and methods of manufacturing semiconductor devices based on the systems and methods of inspecting the DUTs.

2. Description of the Related Art

In a manufacturing process of semiconductor devices or display apparatuses, it is required to detect whether semiconductor substrates on which the semiconductor devices are formed have defects, or whether display panels that are included in the display apparatuses have defects. Recently, an inspection system that obtains images of the semiconductor substrates or the display panels and analyzes the images to detect the defects. As the resolution of machine displayed images increases, and as patterns that are included in the semiconductor substrates or the display panels become more complex and narrow, a greater amount of processing may be required to detect the defects. Thus, researchers are investigating various techniques for developing an inspection system with better performance, e.g., fast inspection speed, accurate and reliable results, etc., and increased scalability and/or flexibility.

SUMMARY

At least one example embodiment of the present disclosure provides an inspection system for a device under test (DUT) capable of efficiently increasing a capacity of processing operations with a relatively low cost.

At least one example embodiment of the present disclosure provides a method of inspecting a device under test (DUT) capable of efficiently increasing a capacity of processing operations with a relatively low cost.

At least one example embodiment of the present disclosure provides a method of manufacturing a semiconductor device based on the method of inspecting the DUT.

According to example embodiments, an inspection system for a device under test (DUT) includes an image sensor, first through N-th image obtaining devices, first through K-th switches, first through M-th image processing devices, and at least one added image processing device, where each of N, K and M is a natural number greater than or equal to two. The image sensor captures an image of the DUT. The first through N-th image obtaining devices is connected to the image sensor, and each of the first through N-th image obtaining devices receives image data of the image of the DUT. Each of the first through K-th switches is connected to a respective one of the first through N-th image obtaining devices. Each of the first through M-th image processing devices is connected to a respective one of the first through K-th switches, receives the image data that is output from one of the first through N-th image obtaining devices and is distributed by one of the first through K-th switches, and generates processed image data by performing a processing operation on the image data in real-time. The at least one added image processing device is connected to one of the first through K-th switches when an additional processing operation for the image data is required, receives the image data, and generates additional processed image data by performing the additional processing operation on the image data in real-time.

According to example embodiments, in a method of inspecting a device under test (DUT), an image of the DUT is captured. Each of first through N-th image obtaining devices receives image data of the image of the DUT, where N is a natural number greater than or equal to two. Each of first through K-th switches distributes the image data output from one of the first through N-th image obtaining devices, where K is a natural number greater than or equal to two. Each of the first through K-th switches is connected to a respective one of the first through N-th image obtaining devices. Each of first through M-th image processing devices generates processed image data by performing a processing operation on the image data in real-time, where M is a natural number greater than or equal to two. Each of the first through M-th image processing devices is connected to a respective one of the first through K-th switches. At least one added image processing device generates additional processed image data by performing an additional processing operation on the image data in real-time when the additional processing operation for the image data is required. The at least one added image processing device is configured to be electrically connectable to one of the first through K-th switches.

According to example embodiments, in a method of manufacturing a semiconductor device, a semiconductor substrate on which the semiconductor device is formed is manufactured. The semiconductor substrate is inspected to determine whether the semiconductor substrate has a defect. In inspecting the semiconductor substrate, an image of the semiconductor substrate is captured. Each of first through N-th image obtaining devices receives image data of the image of the semiconductor substrate, where N is a natural number greater than or equal to two. Each of first through K-th switches distributes the image data output from one of the first through N-th image obtaining devices, where K is a natural number greater than or equal to two. Each of the first through K-th switches is connected to a respective one of the first through N-th image obtaining devices. Each of first through M-th image processing devices generates processed image data by performing a processing operation on the image data in real-time, where M is a natural number greater than or equal to two. Each of the first through M-th image processing devices is connected to a respective one of the first through K-th switches. At least one added image processing device generates additional processed image data by performing an additional processing operation on the image data in real-time when the additional processing operation for the image data is required. The at least one added image processing device is configured to be electrically connectable to one of the first through K-th switches.

In the inspection system and the method of inspecting the DUT according to example embodiments, the image obtaining devices and the image processing devices may be separated from each other. The number of image obtaining devices may be fixed such that a configuration of the image obtaining devices at an initial installation time is always maintained. The number of image processing devices may be variable or flexible such that a configuration of the image processing devices at the initial installation time can be changed and the added image processing device can be used for increasing or expanding the capacities of data processing and/or processing operations after the initial installation time. When the capacities of data processing and/or processing operations of the inspection system are to be increased or expanded after the initial installation time, a single unit (e.g., a single image processing device) may be added to the inspection system, not a single embedded set. Accordingly, the capacities of data processing and/or processing operations may be efficiently increased or expanded with a relatively low cost, thereby enhancing utilization and applicability of the inspection system.

In addition, the data mapping operation, the data distribution operation and the high speed data networking operation may be efficiently performed using the network memories that are included in the image obtaining devices and the image processing devices and the switches that are disposed between the image obtaining devices and the image processing devices, and the amount of processed data in real-time may be efficiently adjusted.

According to one example embodiment, there is an inspection system for a device under test (DUT) including: an image sensor configured to capture an image of the DUT; a first image obtaining device through a N-th image obtaining device connected to the image sensor, wherein N is a first natural number greater than or equal to two, and each of the first image obtaining device through the N-th image obtaining device is configured to receive image data corresponding to the image of the DUT captured by the image sensor; a first switch through a K-th switch, each of which is connected to a respective one of the first image obtaining device through the N-th image obtaining device, wherein K is a second natural number greater than or equal to two; a first image processing device through a M-th image processing device, each of which is connected to a respective one of the first switch through the K-th switch, wherein M is a third natural number greater than or equal to two, each of the first image processing device through the M-th image processing device is configured to: receive the image data that is output from one of the first image obtaining device through the N-th image obtaining device and is distributed by one of the first switch through the K-th switch, and generate a corresponding processed data by performing a processing operation on the image data; and a (M+1)th image processing device connected to one of the first switch through the K-th switch, wherein the (M+1)th image processing device is configured to: receive the image data, and generate additional processed data by performing an additional processing operation on the image data.

According to another example embodiment, there is a method of inspecting a device under test (DUT), including: capturing an image of the DUT; receiving, by each of a first image obtaining device through a N-th image obtaining device, image data of the image of the DUT, where N is a first natural number greater than or equal to two; distributing, by each of a first switch through K-th switch, the image data from one of the first image obtaining device through the N-th image obtaining device, where K is a second natural number greater than or equal to two, each of the first switch through the K-th switch connected to a respective one of the first image obtaining device through the N-th image obtaining device; generating, by each of a first image processing device through a M-th image processing device, processed data by performing a processing operation on the image data, where M is a third natural number greater than or equal to two, each of the first image processing device through the M-th image processing device connected to a respective one of the first switch through the K-th switch; and generating, by a (M+1)th image processing device, additional processed data by performing an additional processing operation on the image data when the additional processing operation for the image data is required, the (M+1)th image processing device configured to be electrically connectable to one of the first switch through the K-th switch.

According to yet another example embodiment, there is a method of manufacturing a semiconductor device, including: manufacturing a semiconductor substrate on which the semiconductor device is formed; and inspecting the semiconductor substrate to determine whether the semiconductor substrate has a defect, the inspecting the semiconductor substrate including: capturing an image of the semiconductor substrate; receiving, by each of a first image obtaining device through a N-th image obtaining device, image data of the image of the semiconductor substrate, where N is a first natural number greater than or equal to two; distributing, by each of a first switch through K-th switch, the image data from one of the first image obtaining device through the N-th image obtaining device, where K is a second natural number greater than or equal to two, each of the first switch through the K-th switch connected to a respective one of the first image obtaining device through the N-th image obtaining device; generating, by each of a first image processing device through a M-th image processing device, processed data by performing a processing operation on the image data, where M is a third natural number greater than or equal to two, each of the first image processing device through the M-th image processing device connected to a respective one of the first switch through the K-th switch; and generating, by a (M+1)th image processing device, additional processed data by performing an additional processing operation on the image data when the additional processing operation for the image data is required, the (M+1)th image processing device configured to be electrically connectable to one of the first switch through the K-th switch.

Additional aspects will be set forth in part in the description which follows and, in part, will be apparent from the description, or may be learned by practice of the presented embodiments.

BRIEF DESCRIPTION OF THE DRAWINGS

The above and other aspects and features of certain embodiments of the present disclosure will be more apparent from the following description taken in conjunction with the accompanying drawings, in which.

DETAILED DESCRIPTION OF THE EMBODIMENTS

Figure 1:
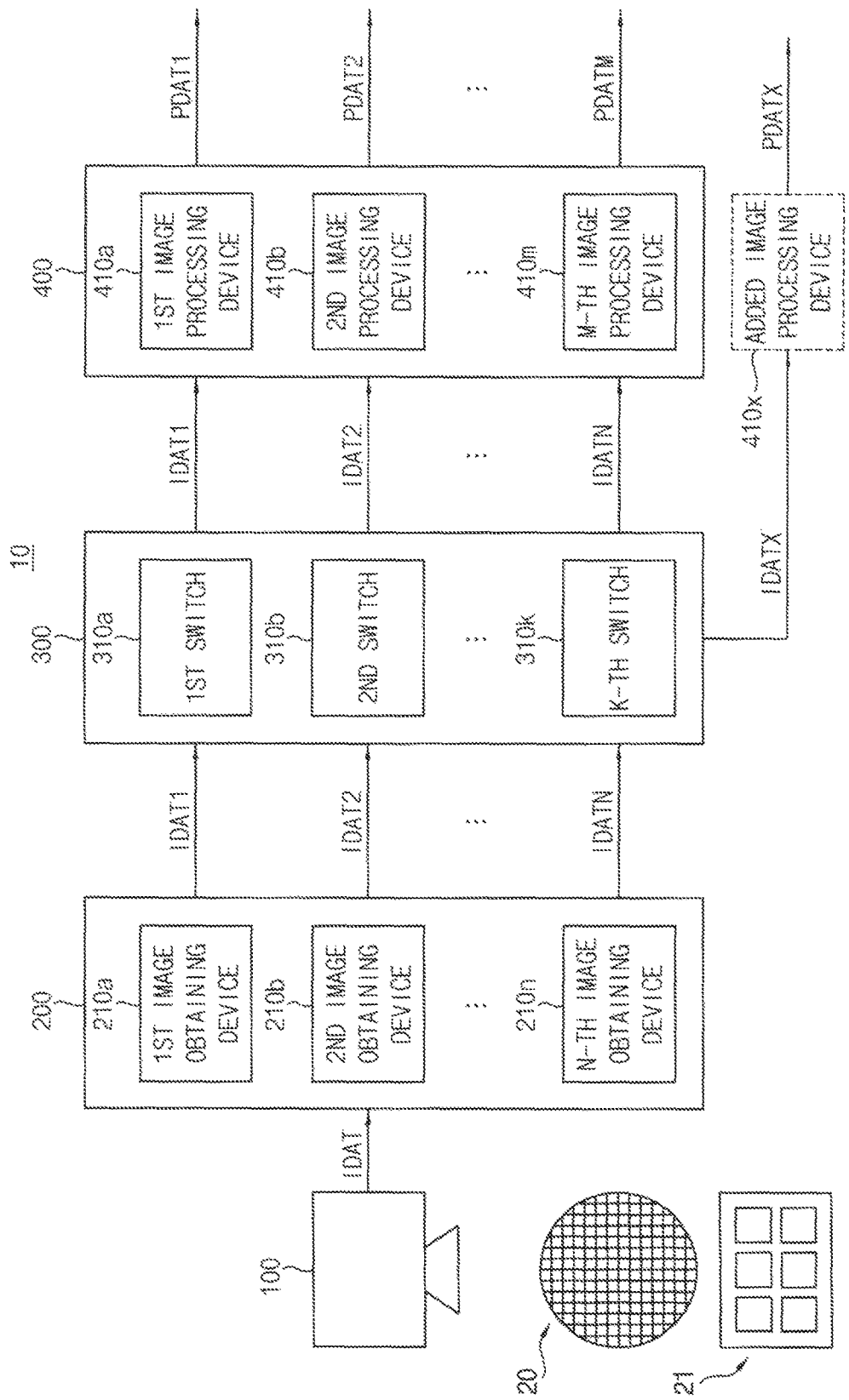
FIG. 1 is a block diagram illustrating an inspection system for a device under test (DUT) according to example embodiments.

Various example embodiments will be described more fully with reference to the accompanying drawings, in which embodiments are shown. The present disclosure may, however, be embodied in many different forms and should not be construed as limited to the embodiments set forth herein. Like reference numerals refer to like elements throughout this application.

FIG. 1 is a block diagram illustrating an inspection system for a device under test (DUT) according to example embodiments.

Referring to FIG. 1, an inspection system 10 for a device under test (DUT) includes an image sensor 100, an image obtaining unit 200, a switch unit 300, an image processing unit 400 and an added image processing device 410x.

The image sensor 100 captures or picks up an image of the DUT. For example, the DUT may include a semiconductor substrate 20 and/or a display panel 21. The semiconductor substrate 20 may represent a semiconductor wafer that is manufactured by, e.g., a mass production, and may include a plurality of semiconductor devices that include a plurality of transistors. The display panel 21 may include a plurality of pixels, a plurality of gate lines and a plurality of data lines. To detect anomalies on the DUT, which represent defects such as scratches, extraneous particles, voids, short circuits, open circuits, etc., the image sensor 100 may capture the image of the DUT to generate image data IDAT of the image of the DUT.

In some example embodiments, the image sensor 100 may include at least one of various types of image sensors such as a charge-coupled device (CCD) image sensor, a complementary metal oxide semiconductor (CMOS) image sensor, or the like. In some example embodiments, the image sensor 100 may be a line image sensor in which the image of the DUT is captured by units of a predetermined line or an area image sensor in which the image of the DUT is captured by units of a predetermined area.

In some example embodiments, each semiconductor device that is included in the semiconductor substrate 20 may include at least one of various types of semiconductor chips such as a central processing unit (CPU), an application processor (AP), or the like. In other example embodiments, each semiconductor device that is included in the semiconductor substrate 20 may include at least one of various types of memory devices such as a dynamic random access memory (DRAM), a flash memory, or the like.

In some example embodiments, the display panel 21 may have rectangular or round edges, and may be included in at least one of various types of display apparatuses such as a liquid crystal display (LCD), an organic light emitting display (OLED), a Quantum dot light emitting display (QLED), or the like.

Although the example embodiments are described based on an example where the DUT includes the semiconductor substrate 20 and/or the display panel 21 (e.g., first DUT, second DUT, etc.), the example embodiments may not be limited thereto, and the DUT includes at least one of various types of devices for detecting anomalies.

The image obtaining unit 200 includes first through N-th image obtaining devices 210a, . . . , 210n, where N is a natural number greater than or equal to two, e.g., first natural number. The first through N-th image obtaining devices 210a, . . . , 210n are connected to the image sensor 100. Each of the first through N-th image obtaining devices 210a, . . . , 210n receives image data of the image of the DUT. As will be described with reference to FIG. 2, each of the first through N-th image obtaining devices 210a, . . . , 210n may include a frame grabber that receives the image data IDAT.

The image data IDAT may include first through N-th image data IDAT1, . . . , IDATN. In this example, the first image obtaining device 210a may receive the first image data IDAT1 from the image sensor 100 and may output the first image data IDAT1, the second image obtaining device 210b may receive the second image data IDAT2 from the image sensor 100 and may output the second image data IDAT2, and the N-th image obtaining device 210n may receive the N-th image data IDATN from the image sensor 100 and may output the N-th image data IDATN. Alternatively, the first image obtaining device 210a may receive the image data IDAT from the image sensor 100 and may extract and output the first image data IDAT1 among the image data IDAT, the second image obtaining device 210b may receive the image data IDAT from the image sensor 100 and may extract and output the second image data IDAT2 among the image data IDAT, and the N-th image obtaining device 210n may receive the image data IDAT from the image sensor 100 and may extract and output the N-th image data IDATN among the image data IDAT.

In some example embodiments, each of the first through N-th image data IDAT1, . . . , IDATN may correspond to a portion of a single DUT. For example, the image data IDAT may correspond to an image of a single semiconductor substrate (e.g., the semiconductor substrate 20), and each of the first through N-th image data IDAT1, . . . , IDATN may correspond to a respective one of first through N-th portions of a single semiconductor substrate.

In other example embodiments, each of the first through N-th image data IDAT1, . . . , IDATN may correspond to a whole of a single DUT. For example, although not illustrated in FIG. 1, the image data IDAT may correspond to first through N-th images of first through N-th semiconductor substrates, and each of the first through N-th image data IDAT1, . . . , IDATN may correspond to a respective one of the first through N-th semiconductor substrates (e.g., a respective one of the first through N-th images).

In still other example embodiments, the first through N-th image data IDAT1, . . . , IDATN may be substantially the same as each other. In other words, the first through N-th image obtaining devices 210a, . . . , 210n may receive the same image data from the image sensor 100 and may output the same image data.

Although not described in detail, a configuration of the first through N-th image data IDAT1, . . . , IDATN may be changed according to example embodiments.

The switch unit 300 includes first through K-th switches 310a, . . . , 310k, where K is a natural number greater than or equal to two, e.g., second natural number. Each of the first through K-th switches 310a, . . . , 310k is connected to a respective one of or at least one of the first through N-th image obtaining devices 210a, . . . , 210n. For example, if K is equal to N (e.g., K=N), one image obtaining device and one switch may be connected to each other based on a one-to-one correspondence. In this example, the first switch 310a may be connected to the first image obtaining device 210a, the second switch 310b may be connected to the second image obtaining device 210b, and the K-th switch 310k may be connected to the N-th image obtaining device 210n. For another example, if K is not equal to N, two or more image obtaining devices may be connected to one switch, or one image obtaining device may be connected to two or more switches.

The image processing unit 400 includes first through M-th image processing devices 410a, . . . , 410m, where M is a natural number greater than or equal to two, e.g., a third natural number. Each of the first through M-th image processing devices 410a, . . . , 410m is connected to a respective one of the first through K-th switches 310a, . . . , 310k, receives the image data that is output from one of the first through N-th image obtaining devices 210a, . . . , 210n and is distributed (or allocated or in an operation of distributing) by one of the first through K-th switches 310a, . . . , 310k, and generates processed image data, e.g., processed data or corresponding processed data, by performing a processing operation on the image data in real-time (or during runtime). In an exemplary embodiment each of the first through M-th image processing devices 410a, . . . , 410m performs a generating operation to generate processed image data. As will be described with reference to FIG. 2, each of the first through M-th image processing devices 410a, . . . , 410m may include at least one graphic processing unit (GPU).

In some example embodiments, the number of the first through N-th image obtaining devices 210a, . . . , 210n, e.g., a first number, may be different from the number of the first through M-th image processing devices 410a, . . . , 410m, e.g., a second number. For example, the number of the first through M-th image processing devices 410a, . . . , 410m may be greater than the number of the first through N-th image obtaining devices 210a, . . . , 210n. In other words, the natural numbers N and M may be different from each other, e.g., M may be greater than N.

Resolution of machine for displaying the image of the DUT increases, and patterns that are included in the semiconductor substrate 20 and/or the display panel 21 become more complex and narrow. However, since resolution of the image sensor 100 for capturing the image of the DUT can not meet the resolution of machine for displaying the image of the DUT, there are some limits to detect and classify defects on the semiconductor substrate 20 and/or the display panel 21. For this reason, to accurately and precisely detect the defects on the semiconductor substrate 20 and/or the display panel 21, a greater amount of the processed image data generated by the image processing unit 400 may be required. For example, the amount of the processed image data may be much greater than (e.g., more than several times) the amount of the image data (e.g., the image data IDAT) obtained by the image sensor 100. Accordingly, in the inspection system 10 according to example embodiments, the number of the first through M-th image processing devices 410a, . . . , 410m may be greater than the number of the first through N-th image obtaining devices 210a, . . . , 210n.

In other words, in the inspection system 10 according to example embodiments, one image obtaining device may correspond to (e.g., may be connected to) two or more image processing devices. A switch that is connected to one image obtaining device may distribute image data that is output from one image obtaining device and may provide the distributed data to two or more image processing devices.

For example, the first image processing device 410a may be connected to the first switch 310a, may receive some or all of the first image data IDAT1 that is output from the first image obtaining device 210a and is distributed by the first switch 310a, and may generate first processed image data PDAT1 by performing a first processing operation on some or all of the first image data IDAT1 in real-time. The second image processing device 410b may be connected to the first switch 310a, may receive some or all of the first image data IDAT1 that is output from the first image obtaining device 210a and is distributed by the first switch 310a, and may generate second processed image data PDAT2 by performing a second processing operation on some or all of the first image data IDAT1 in real-time. Similarly, the M-th image processing device 410m may be connected to the K-th switch 310k, may receive some or all of the N-th image data IDATN that is output from the N-th image obtaining device 210n and is distributed by the K-th switch 310k, and may generate M-th processed image data PDATM by performing a M-th processing operation on some or all of the N-th image data IDATN in real-time.

The added image processing device 410x, e.g., (M+1)th image processing device, is configured to be electrically connectable to one of the first through K-th switches 310a, . . . , 310k. When an additional processing operation for some or all of the image data IDAT is required, the added image processing device 410x is connected to one of the first through K-th switches 310a, . . . , 310k, receives the image data that is output from one of the first through N-th image obtaining devices 210a, . . . , 210n and is distributed by one of the first through K-th switches 310a, . . . , 310k, and generates additional processed image data PDATX, e.g., additional processed data, by performing the additional processing operation on the image data in real-time, e.g., first additional processing operation. The added image processing device 410x may be used for increasing or expanding capacities of data processing and/or processing operations of the inspection system 10.

Although FIG. 1 illustrates a single added image processing device 410x, the example embodiments may not be limited thereto, and the inspection system 10 may include a plurality of added image processing devices according to example embodiments. In other words, the inspection system 10 may include at least one added image processing device.

In a conventional inspection system, image obtaining devices and image processing devices were implemented as a single embedded equipment (e.g., a single embedded set). When capacities of data processing and/or processing operations of the conventional inspection system are to be increased or expanded after an initial installation time, another embedded equipment including a plurality of image obtaining devices and image processing devices should be added. Thus, the conventional inspection system has a problem with relatively high cost and many changes for increasing or expanding the capacities of data processing and/or processing operations.

In the inspection system 10 according to example embodiments, the image obtaining devices 210a, 210b, . . . , 210n and the image processing devices 410a, 410b, . . . , 410m may be separated from each other. The number of image obtaining devices may be fixed such that a configuration of the image obtaining devices 210a, 210b, . . . , 210n at an initial installation time is always maintained. The number of image processing devices may be variable or flexible such that a configuration of the image processing devices 410a, 410b, . . . , 410m at the initial installation time can be changed and the added image processing device 410x can be used for increasing or expanding the capacities of data processing and/or processing operations after the initial installation time.

For example, at the initial installation time, the inspection system 10 may include N image obtaining devices 210a, 210b, . . . , 210n and M image processing devices 410a, 410b, . . . , 410m. While the inspection system 10 actually works after the initial installation time, at least one added image processing device 410x may be additionally connected to the inspection system 10 as needed. In other words, when the capacities of data processing and/or processing operations of the inspection system 10 are to be increased or expanded after the initial installation time, a single unit (e.g., a single image processing device) may be added to the inspection system 10, not a single embedded set. Accordingly, the capacities of data processing and/or processing operations may be efficiently increased or expanded with a relatively low cost, thereby enhancing utilization and applicability of the inspection system 10.

Figure 2:
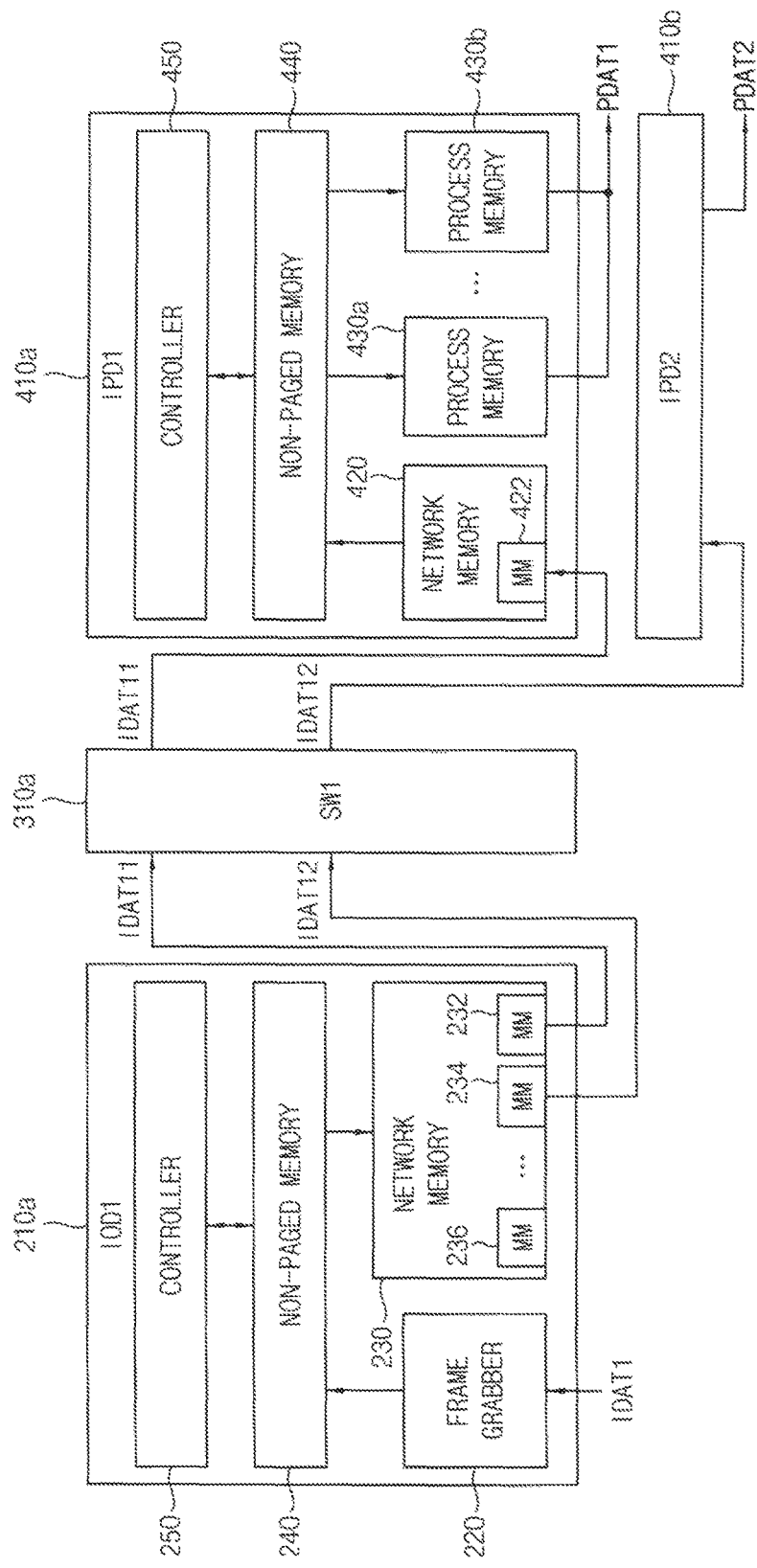
FIGS. 2 and 3 are block diagrams illustrating an example of image obtaining devices, switches and image processing devices that are included in the inspection system of FIG. 1.
Figure 3:
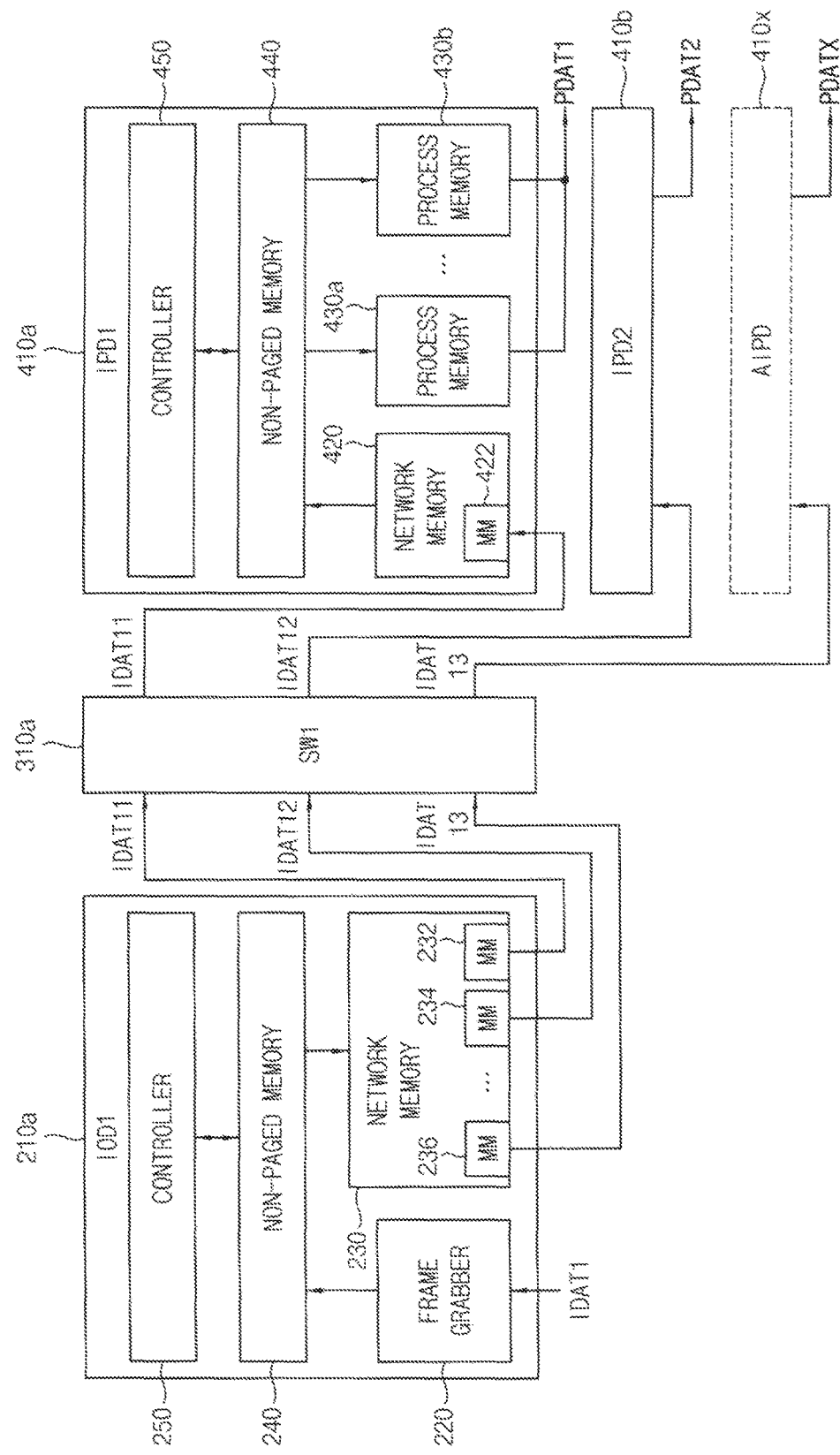

FIGS. 2 and 3 are block diagrams illustrating an example of image obtaining devices, switches and image processing devices that are included in the inspection system of FIG. 1. For convenience of illustration, one image obtaining device 210a, two image processing devices 410a and 410b, one added image processing device 410x and one switch 310a are only illustrated in FIGS. 2 and 3.

Referring to FIGS. 1 and 2, at an initial installation time of the inspection system 10, the first image processing device (IPD1) 410a and the second image processing device (IPD2) 410b may be connected to the first image obtaining device (IOD1) 210a via the first switch (SW1) 310a.

The first image obtaining device 210a may receive the first image data IDAT1 from the image sensor 100.

The first image obtaining device 210a may include a frame grabber 220, a network memory 230 and a non-paged memory 240. The first image obtaining device 210a may further include a controller 250.

The first image obtaining device 210a may start an operation based on an inspection start signal. For example, the inspection start signal may be activated based on an external sensing by an external sensor. For another example, the inspection start signal may be activated based on an internal sensing, which is performed by detecting change of images in an always capture mode.

The frame grabber 220 may receive the first image data IDAT1 from the image sensor 100 based on a first communication protocol. In some example embodiments, the first communication protocol may include a peripheral component interconnect (PCI) or a PCI express (PCIe). In other example embodiments, the first communication protocol may include a serial advanced technology attachment (SATA), a SATA express (SATAe) or a SAS (serial attached small computer system interface (SCSI)). In still example embodiments, the first communication protocol may include an interface that is communicable with a computer, e.g., a universal serial bus (USB).

The network memory 230 may output first and second image sub-data IDAT11 and IDAT12, each of which corresponds to some of all of the first image data IDAT1, based on the first communication protocol. In other words, a data receiving (or inputting) interface and a data transmitting (or outputting) interface of the first image obtaining device 210a may be substantially the same as each other.

The network memory 230 may include a plurality of mapping memories (MM) 232, 234 and 236. The first image sub-data IDAT11 may be output from the mapping memory 232, and the second image sub-data IDAT12 may be output from the mapping memory 234.

The non-paged memory 240 may control a data transmission between the frame grabber 220 and the network memory 230 in the first image obtaining device 210a based on a second communication protocol. The second communication protocol may be different from the first communication protocol. In other words, an external data interface and an internal data interface of the first image obtaining device 210a may be different from each other.

The controller 250 may control overall operations of the first image obtaining device 210a. For example, the controller 250 may execute an application program (e.g., a software) to drive the first image obtaining device 210a, and the data transmission operation described above may be performed by the application program.

The first switch 310a may distribute the first and second image sub-data IDAT11 and IDAT12, each of which corresponds to some of all of the first image data IDAT1 output from the first image obtaining device 210a.

The first image processing device 410a may receive the first image sub-data IDAT11 that corresponds to some of all of the first image data IDAT1 and is distributed by the first switch 310a, and may generate the first processed image data PDAT1 by performing the first processing operation on the first image sub-data IDAT11.

The first image processing device 410a may include a network memory 420, at least one processing memory 430a, . . . , 430b and a non-paged memory 440. The first image processing device 410a may further include a controller 450.

The network memory 420 may receive the first image sub-data IDAT11 based on the first communication protocol. In other words, a data receiving (or inputting) interface of the first image processing device 410a may be substantially the same as the data receiving interface and the data transmitting interface of the first image obtaining device 210a.

The network memory 420 may include at least one mapping memory 422. The first image sub-data IDAT11 may be received by the at least one mapping memory 422.

The at least one processing memory 430a, . . . 430b may perform the first processing operation on the first image sub-data IDAT11, and may generate the first processed image data PDAT1 as a result of the first processing operation. For example, the at least one processing memory 430a, . . . 430b may include a GPU.

The non-paged memory 440 may control a data transmission between the network memory 420 and the at least one processing memory 430a, . . . 430b in the first image processing device 410a based on the second communication protocol that is different from the first communication protocol. In other words, an internal data interface of the first image processing device 410a may be substantially the same as the internal data interface of the first image obtaining device 210a.

The controller 450 may control overall operations of the first image processing device 410a. For example, the controller 450 may execute an application program to drive the first image processing device 410a, and the data transmission operation described above may be performed by the application program. For example, the controller 450 may include a CPU.

The second image processing device 410b may receive the second image sub-data IDAT12 that corresponds to some of all of the first image data IDAT1 and is distributed by the first switch 310a, and may generate the second processed image data PDAT2 by performing the second processing operation on the second image sub-data IDAT12. According to example embodiments, the second processing operation may be substantially the same as or different from the first processing operation.

Although not illustrated in FIG. 2 in detail, a structure of the second image processing device 410b may be substantially the same as a structure of the first image processing device 410a. For example, the second image processing device 410b may include a network memory, at least one processing memory and a non-paged memory, and may further include a controller.

In some example embodiments, the first image sub-data IDAT11 and the second image sub-data IDAT12 may be substantially the same as each other, and each of the first and second image sub-data IDAT11 and IDAT12 may correspond to all of the first image data IDAT1. In this example, the first switch 310a may sequentially provide the first and second image sub-data IDAT11 and IDAT12 to the first and second image processing devices 410a and 410b, respectively.

In other example embodiments, the first image sub-data IDAT11 and the second image sub-data IDAT12 may be different from each other. For example, the first image sub-data IDAT11 may correspond to a first portion of the first image data IDAT1 and the second image sub-data IDAT12 may correspond to a second portion of the first image data IDAT1. In this example, the first switch 310a may substantially simultaneously or concurrently provide the first and second image sub-data IDAT11 and IDAT12 to the first and second image processing devices 410a and 410b, respectively.

In still other example embodiments, implementation of the first and second image sub-data IDAT11 and IDAT12 and data distribution scheme of the first switch 310a may be changed according to example embodiments.

The data mapping operation, the data distribution operation and the high speed data networking operation may be efficiently performed according to the operations of the first image obtaining device 210a, the first switch 310a and the first and second image processing devices 410a and 410b (e.g., according to data flow via the network memories 230 and 420 and the first switch 310a).

Although not illustrated in FIG. 2 in detail, a structure of each of the second through N-th image obtaining devices 210b, . . . , 210n may be substantially the same as a structure of the first image obtaining device 210a, and a structure of each image processing device among the first through M-th image processing devices 410a, . . . , 410m other than the first and second image processing devices 410a and 410b may be substantially the same as the structure of the first image processing device 410a.

In some example embodiments, the number of image processing devices connected to one image obtaining device may be the same as each other for all of the image obtaining devices 210a, 210b, . . . , 210n. For example, when the first image obtaining device 210a is connected to the first and second image processing devices 410a and 410b as illustrated in FIG. 2, the second image obtaining device 210b may be connected to third and fourth image processing devices via the second switch 310b, and the N-th image obtaining device 210n may be connected to (M−1)-th and M-th image processing devices 410m via the K-th switch 310k. In other words, M=Z*N where Z is a natural number greater than or equal to two, and Z=2 in an example of FIG. 2.

In other example embodiments, the number of image processing devices connected to one image obtaining device may be different from each other for all of the image obtaining devices 210a, 210b, . . . , 210n. For example, when the first image obtaining device 210a is connected to the first and second image processing devices 410a and 410b as illustrated in FIG. 2, the second image obtaining device 210b may be connected to third, fourth and fifth image processing devices via the second switch 310b. In other words, M may be any natural number greater than N.

In still other example embodiments, the number of image processing devices connected to one image obtaining device may be changed according to example embodiments.

Referring to FIGS. 1 and 3, after the initial installation time, e.g., after the inspection system 10 is installed with N image obtaining devices 210a, 210b, . . . , 210n and M image processing devices 410a, 410b, . . . , 410m, it may be required to increase or expand the capacities of data processing and/or processing operations of the inspection system 10. For example, the additional processing operation for the first image data IDAT1 that is received by the first image obtaining device 210a may be required. Thus, the added image processing device (AIPD) 410x, which is configured to be electrically connectable to the first switch 310a, may be connected to the first image obtaining device 210a via the first switch 310a to increase or expand the capacities of data processing and/or processing operations for the first image data IDAT1.

In some example embodiments, the first switch 310a may include two slots for the first and second image processing devices 410a and 410b and at least one expansion slot for the added image processing device 410x. In an example of FIG. 2, the at least one expansion slot may be empty. In an example of FIG. 3, when the added image processing device 410x is used for increasing or expanding the capacities of data processing and/or processing operations, the added image processing device 410x may be connected to the first switch 310a via the at least one expansion slot.

In other example embodiments, the first switch 310a may include two connection cables for the first and second image processing devices 410a and 410b and at least one expansion connection cable for the added image processing device 410x. In an example of FIG. 2, the at least one expansion connection cable may be empty. In an example of FIG. 3, when the added image processing device 410x is used for increasing or expanding the capacities of data processing and/or processing operations, the added image processing device 410x may be connected to the first switch 310a via the at least one expansion connection cable.

In still other example embodiments, the first switch 310a may include any structure (e.g., a plug-in connection) for the added image processing device 410x such that the added image processing device 410x is connected to the first switch 310a via the structure.

Although not illustrated in FIG. 3 in detail, a structure of the added image processing device 410x may be substantially the same as the structure of each of the first and second image processing device 410a and 410b. For example, the added image processing device 410x may include a network memory, at least one processing memory and a non-paged memory, and may further include a controller.

In some example embodiments, when the added image processing device 410x is additionally connected to the inspection system 10, the data mapping operation, the data distribution operation and the high speed data networking operation described with reference to FIG. 2 may be partially changed by user setting. For example, the network memory 230 may output the first, second and third image sub-data IDAT11, IDAT12 and IDAT13, each of which corresponds to some of all of the first image data IDAT1, based on the first communication protocol. The first image sub-data IDAT11 may be output from the mapping memory 232, the second image sub-data IDAT12 may be output from the mapping memory 234, and the third image sub-data IDAT13 may be output from the mapping memory 236. The first switch 310a may distribute the first, second and third image sub-data IDAT11, IDAT12 and IDAT13. When the added image processing device 410x is connected to the first switch 310a, the added image processing device 410x may receive the third image sub-data IDAT13 that corresponds to some of all of the first image data IDAT1 and is distributed by the first switch 310a, and may generate the additional processed image data PDATX by performing the additional processing operation on the third image sub-data IDAT13. As described with reference to FIG. 2, the first, second and third image sub-data IDAT11, IDAT12 and IDAT13 may be substantially the same as or different from each other, and the additional processing operation and the first and second processing operations may be substantially the same as or different from each other.

Although not illustrated in FIG. 3 in detail, the number of the added image processing devices may be changed according to example embodiments.

In some example embodiments, one added image processing device may be connected for every image obtaining device. For example, (N−1) added image processing devices, each of which is configured to be electrically connectable to one of the second through K-th switches 310b, . . . , 310k, may be further used for increasing or expanding the capacities of data processing and/or processing operations. In other words, the inspection system 10 may further include N added image processing devices.

In other example embodiments, one added image processing device may be connected for only one image obtaining device. For example, as illustrated in FIG. 3, the inspection system 10 may only include the added image processing device 410x that is connected to the first image obtaining device 210a.

In still other example embodiments, two or more added image processing devices may be connected for one image obtaining device.

Figure 4:
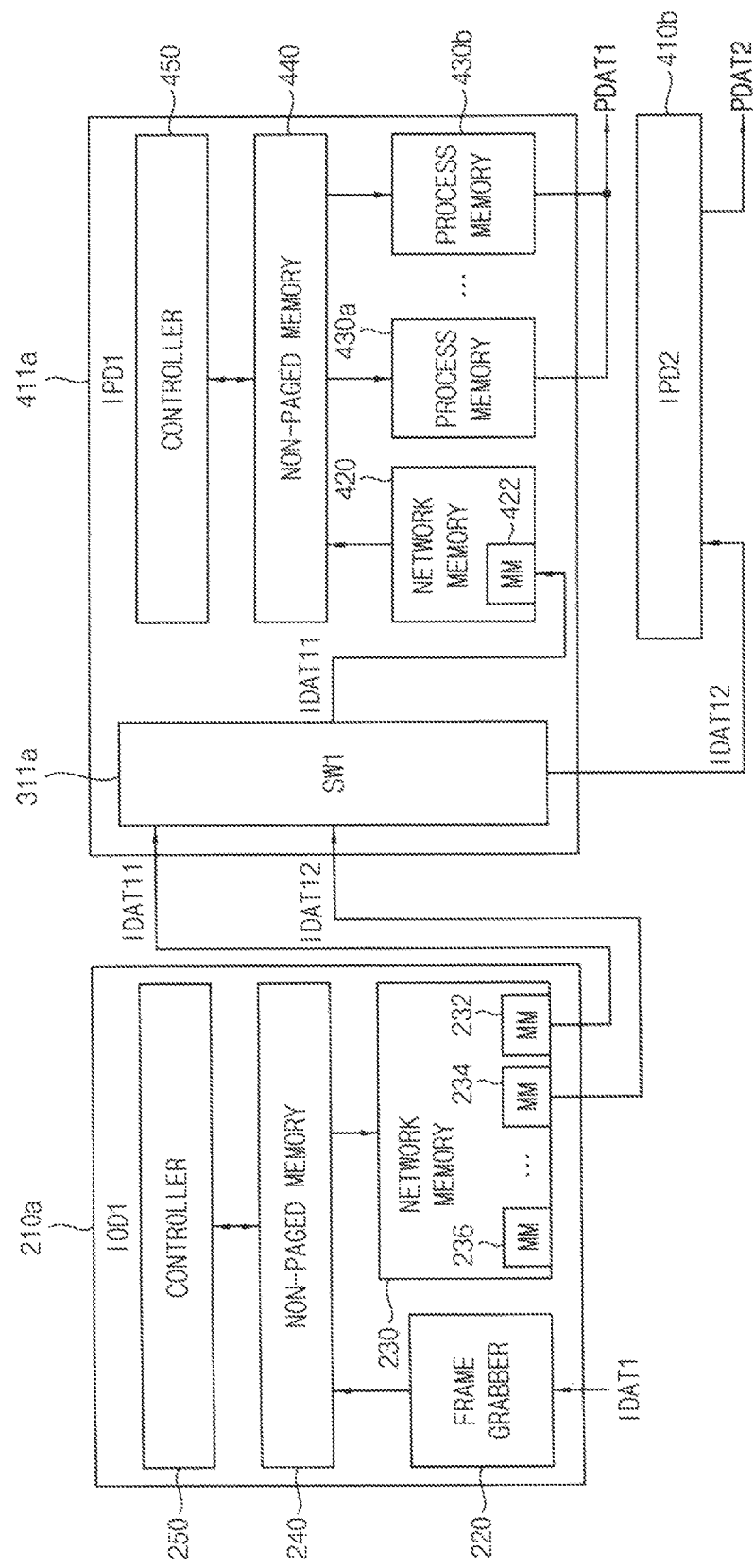
FIGS. 4 and 5 are block diagrams illustrating another example of image obtaining devices, switches and image processing devices that are included in the inspection system of FIG. 1.
Figure 5:
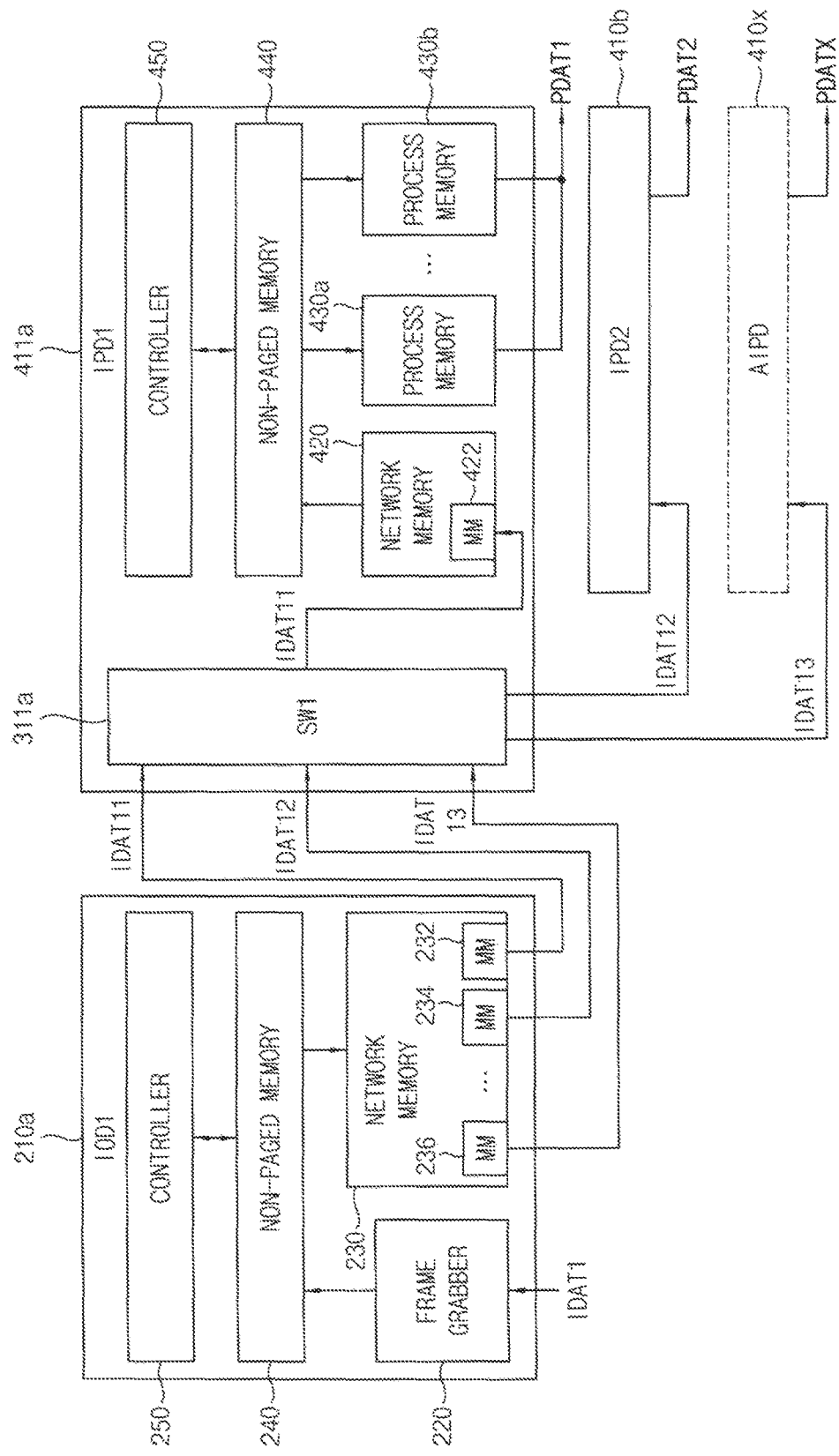

FIGS. 4 and 5 are block diagrams illustrating another example of image obtaining devices, switches and image processing devices that are included in the inspection system of FIG. 1.

Referring to FIGS. 1, 4 and 5, an example of FIGS. 4 and 5 may be substantially the same as an example of FIGS. 2 and 3, except that a first switch 311a is located or disposed inside a first image processing device 411a in FIGS. 4 and 5. Thus, repeated explanation will be omitted.

Although not illustrated in FIGS. 4 and 5, the first switch may be located or disposed inside the second image processing device 410b. In other words, the first switch may be located or disposed inside one of the first and second image processing devices. In addition, although not illustrated in FIGS. 4 and 5, each of the second through K-th switches 310b, . . . , 310k may also be located or disposed inside a respective image processing device.

Figure 6:
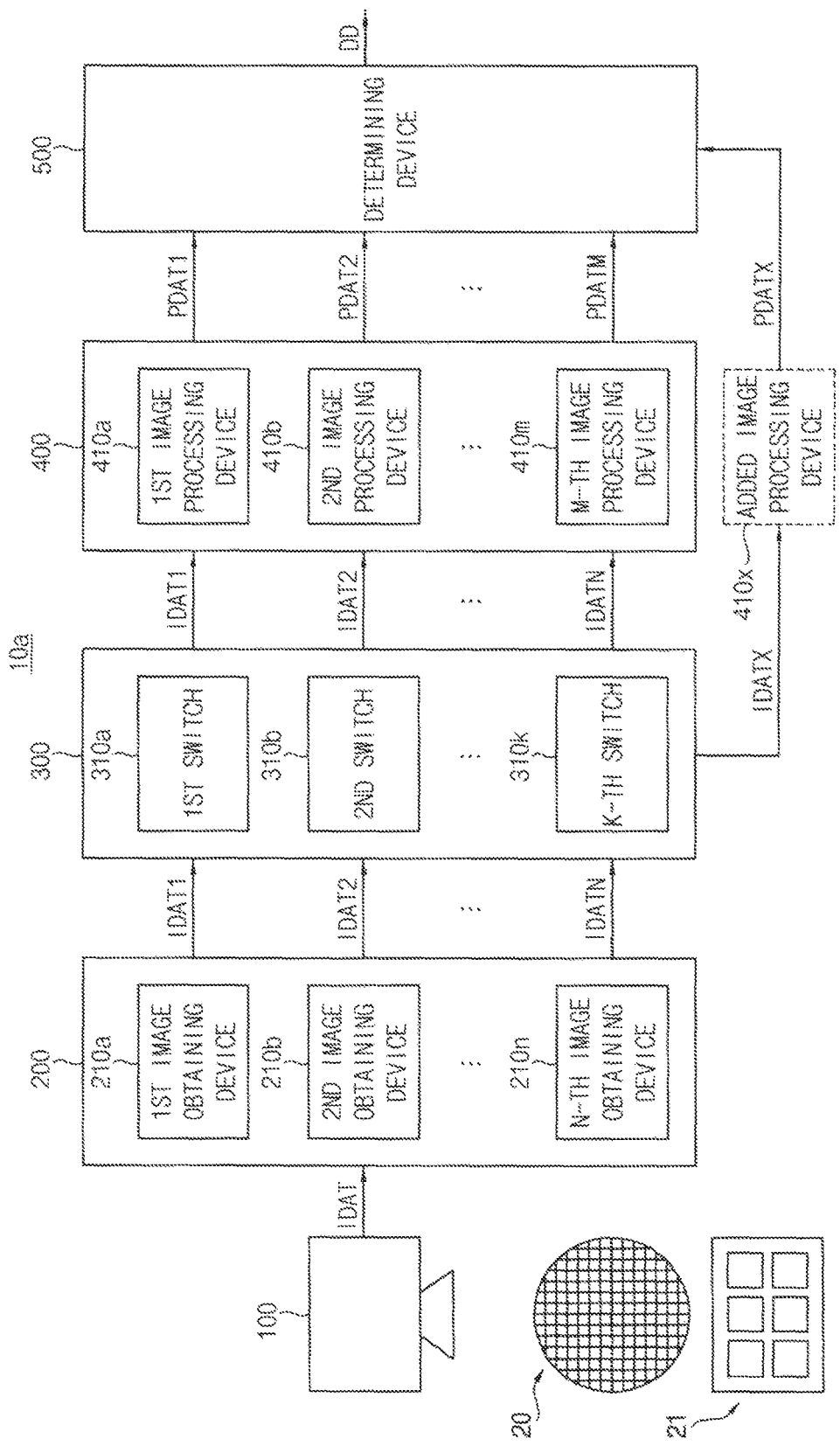
FIG. 6 is a block diagram illustrating an inspection system for a DUT according to example embodiments.

FIG. 6 is a block diagram illustrating an inspection system for a DUT according to example embodiments.

An example of FIG. 6 may be substantially the same as an example of FIG. 1, except that an inspection system 10a of FIG. 6 further includes a determining device 500. Thus, repeated explanation will be omitted.

Referring to FIG. 6, the determining device 500 may determine whether the DUT (e.g., the semiconductor substrate 20 and/or the display panel 21) has a defect based on at least one of the processed image data PDAT1, PDAT2, . . . , PDATM and the additional processed image data PDATX, and may generate determined data DD that represents a result of the determining operation. For example, at the initial installation time in which the added image processing device 410x is not connected to the inspection system 10a, the determining device 500 may determine whether the DUT has the defect based on the processed image data PDAT1, PDAT2, . . . , PDATM. After the added image processing device 410x is connected to the inspection system 10a, the determining device 500 may determine whether the DUT has the defect based on both the processed image data PDAT1, PDAT2, . . . , PDATM and the additional processed image data PDATX.

In some example embodiments, the determining device 500 may determine whether the DUT (e.g., the semiconductor substrate 20 and/or the display panel 21) has the defect based on a machine learning or a deep learning. The machine learning or the deep learning may represent a learning process based on an artificial neural network (ANN). The ANN is obtained by engineering a cell structure model of a human brain where a process of efficiently recognizing a pattern is performed. The ANN refers to a calculation model that is based on software or hardware and is designed to imitate biological calculation abilities by applying many artificial neurons interconnected through connection lines. The human brain consists of neurons that are basic units of a nerve, and encrypts or decrypts information according to different types of dense connections between these neurons. Artificial neurons in the ANN are obtained through simplification of biological neuron functionality. The image processing devices 410a, 410b, . . . , 410m and 410x may perform statistical image composition and/or learning-based image processing based on design information, a reference image, etc. The determining device 500 may input a result of the image processing devices 410a, 410b, . . . , 410m and 410x to the ANN, and may generate output data (e.g., the determined data DD), by the ANN, for determining whether the DUT has the defect.

In other example embodiments, the determining device 500 may manually determine whether the DUT (e.g., the semiconductor substrate 20 and/or the display panel 21) has the defect.

In the inspection system 10 and inspection system 10a according to example embodiments, the number (e.g., N) of the first through N-th image obtaining devices 210a, . . . , 210n and the number (e.g., M) of the first through M-th image processing devices 410a, . . . , 410m may be determined based on the amount of image data provided from the image sensor 100, data transmission speed of the first through N-th image obtaining devices 210a, . . . , 210n, and processing speed of the first through M-th image processing devices 410a, . . . , 410m.

Firstly, the amount of image data provided from the image sensor 100 may be checked. For example, when the image sensor 100 is a line image sensor, the total amount of image data may be obtained by multiplying the total number of pixels, the number of processed bits and the number of lines. Alternatively, when the image sensor 100 is an area image sensor, the total amount of image data may be obtained by multiplying the total number of pixels and the number of processed bits. After then, data receiving and transmitting speed (e.g., specification of inputting and outputting speed) of the image obtaining devices 210a, 210b, . . . , 210n may be checked, and thus the image obtaining unit 200 (e.g., a fixed part) including the image obtaining devices 210a, 210b, . . . , 210n may be designed. In the example embodiments, data receiving and data transmitting speeds may be the same or different for each of the image obtaining devices 210a, 210b, ..., 210n. After then, data distribution scheme may be determined based on the processing speed, a structure for additionally connecting the added image processing device 410x may be determined, and thus the image processing unit 400 (e.g., a variable part) including the image processing devices 410a, 410b, ..., 410m and the switch unit 300 may be designed.

In the inspection system 10 and inspection system 10a according to example embodiments, the image obtaining devices 210a, 210b, ..., 210n including the frame grabber and the image processing devices 410a, 410b, ..., 410m including the GPU and/or CPU may be physically separated from each other. When the capacities of data processing and/or processing operations are to be increased or expanded, the added image processing device 410x may only be additionally connected to the inspection system 10 and inspection system 10a, and thus performance of the inspection system 10 and inspection system 10a may be efficiently enhanced. In addition, the data mapping operation, the data distribution operation and the high speed data networking operation may be efficiently performed using the network memories 230 and 420 and the switches 310a, 310b, ..., 310k, and the amount of processed data in real-time may be efficiently adjusted.

The present disclosure may be employed to examples where the number of switches 310a, 310b, ..., 310k and the number of image obtaining devices 210a, 210b, ..., 210n are the same as and different from each other.

Figure 7:
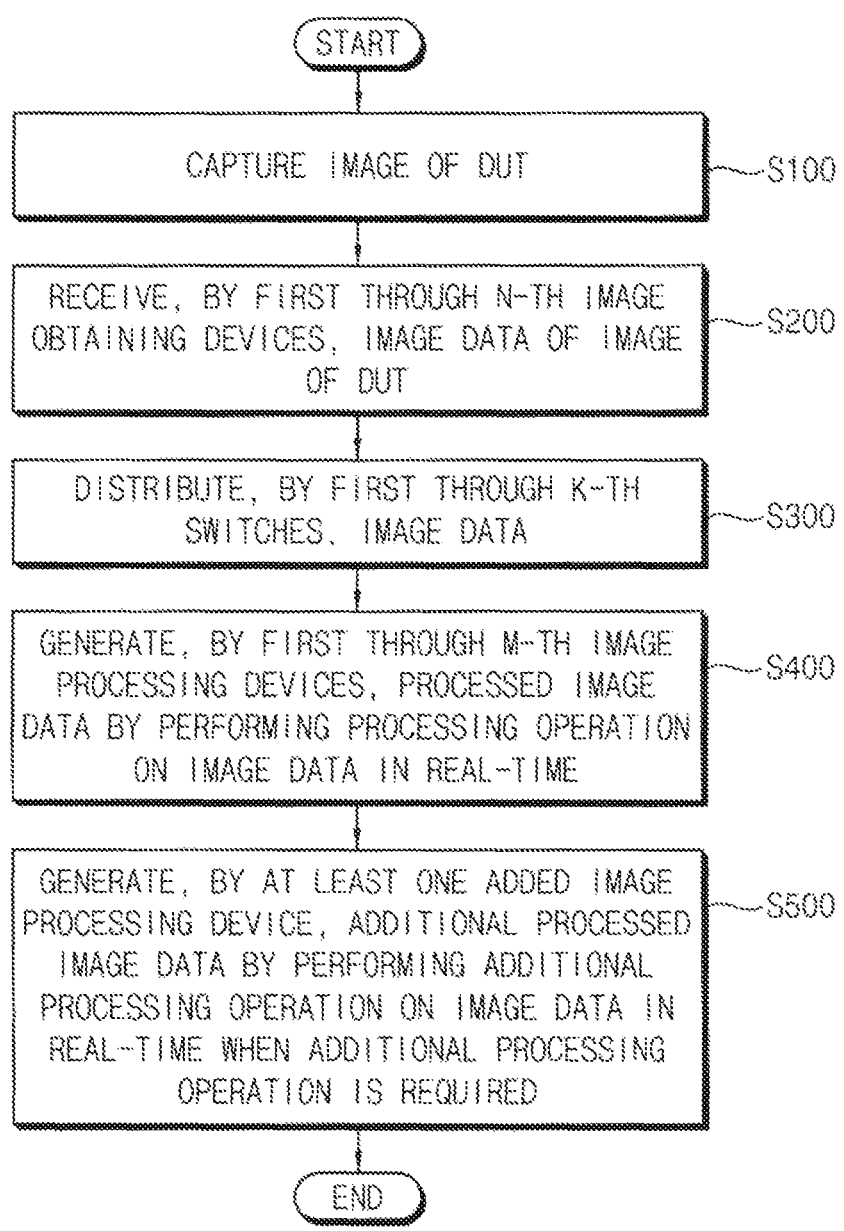
FIG. 7 is a flow chart illustrating a method of inspecting a DUT according to example embodiments.

FIG. 7 is a flow chart illustrating a method of inspecting a DUT according to example embodiments.

Referring to FIGS. 1 and 7, in a method of inspecting a DUT according to example embodiments, the image sensor 100 captures an image of the DUT (e.g., the semiconductor substrate 20 and/or the display panel 21) (operation S100). Each of the first through N-th image obtaining devices 210a, ..., 210n receives the image data IDAT of the image of the DUT (operation S200). For example, the image data IDAT may include the first through N-th image data IDAT1, ..., IDATN. Each of the first through N-th image obtaining devices 210a, ..., 210n may receive and output a respective one of the first through N-th image data IDAT1, ..., IDATN.

Each of the first through K-th switches 310a, ..., 310k, which is connected to a respective one of the first through N-th image obtaining devices 210a, ..., 210n, distributes the image data output from a respective one of the first through N-th image obtaining devices 210a, ..., 210n (operation S300). For example, each of the first through K-th switches 310a, ..., 310k may distribute a respective one of the first through N-th image data IDAT1, ..., IDATN that are output from the first through N-th image obtaining devices 210a, ..., 210n.

Each of the first through M-th image processing devices 410a, ..., 410m, which is connected to a respective one of the first through K-th switches 310a, ..., 310k, generates the processed image data by performing a processing operation on the image data in real-time (operation S400). For example, each of the first through M-th image processing devices 410a, ..., 410m may receive a respective one of the first through N-th image data IDAT1, ..., IDATN that are distributed by the first through K-th switches 310a, ..., 310k, and may generate a respective one of the first through M-th processed image data PDAT1, PDAT2, ..., PDATM by performing the processing operation on a respective one of the first through N-th image data IDAT1, ..., IDATN in real-time.

When the additional processing operation for the image data is required, the at least one added image processing device 410x generates the additional processed image PDATX data by performing the additional processing operation on the image data in real-time (operation S500). The added image processing device 410x is configured to be electrically connectable to one of the first through K-th switches 310a, ..., 310k. To perform operation S500, the number of image obtaining devices may be fixed such that a configuration of the image obtaining devices 210a, 210b, ..., 210n at an initial installation time is always maintained, and the number of image processing devices may be variable or flexible such that a configuration of the image processing devices 410a, 410b, ..., 410m at the initial installation time can be changed and the added image processing device 410x can be used for increasing or expanding the capacities of data processing and/or processing operations after the initial installation time.

In some example embodiments, at least a part of the inspection system and/or the method of inspecting the DUT may be implemented as hardware. For example, at least a part of the inspection system and/or the method of inspecting the DUT may be included in a computer-based electronic system. In other example embodiments, at least a part of the inspection system and/or the method of inspecting the DUT may be implemented as instructions or program routines (e.g., a software program). For example, the instructions or the program routines may be executed by a processing unit, and may be stored in a storage or a memory device.

Figure 8:
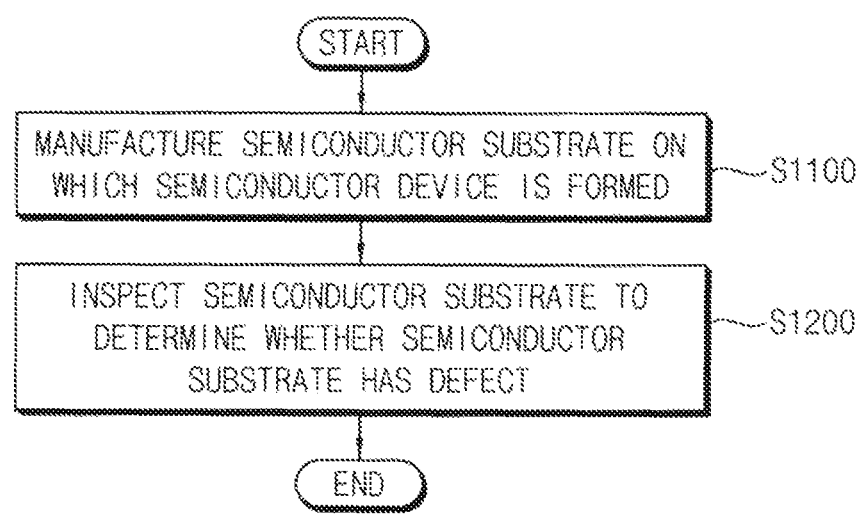
FIG. 8 is a flow chart illustrating a method of manufacturing a semiconductor device according to example embodiments.

FIG. 8 is a flow chart illustrating a method of manufacturing a semiconductor device according to example embodiments.

Referring to FIG. 8, in a method of manufacturing a semiconductor device according to example embodiments, a semiconductor substrate on which the semiconductor device is formed is manufactured (operation S1100). For example, the semiconductor device may include at least one of various types of semiconductor chips such as a CPU, an AP, or the like. For another example, the semiconductor device may include at least one of various types of memory devices such as a DRAM, a flash memory, or the like.

The semiconductor substrate is inspected to determine whether the semiconductor substrate has a defect (operation S1200). Operation S1200 may include operations S100, S200, S300, S400 and S500 in FIG. 7, and thus repeated explanation will be omitted.

Although FIG. 8 illustrates the method of manufacturing the semiconductor device, the present disclosure may be employed to various embodiments of manufacturing a display apparatus, any DUT, etc.

As will be appreciated by those skilled in the art, the present disclosure may be embodied as a system, method, computer program product, and/or a computer program product embodied in one or more computer readable medium(s) having computer readable program code embodied thereon. The computer readable program code may be provided to a processor of a general purpose computer, special purpose computer, or other programmable data processing apparatus. The computer readable medium may be a computer readable signal medium or a computer readable storage medium. The computer readable storage medium may be any tangible medium that can contain, or store a program for use by or in connection with an instruction execution system, apparatus, or device. For example, the computer readable medium may be a non-transitory computer readable medium.

The present disclosure may be applied in a manufacturing process of various types of semiconductor devices and/or display apparatuses, and more particularly in an inspection of a mass production process to detect whether semiconductor substrates on which the semiconductor devices are formed have some defects or not, and/or whether display panels that are included in the display apparatuses have some defects or not.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present disclosure. Accordingly, all such modifications are intended to be included within the scope of the present disclosure as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An inspection system for a device under test (DUT) comprising:
   an image sensor configured to capture an image of the DUT;
   a first image obtaining device through a N-th image obtaining device connected to the image sensor, wherein N is a first natural number greater than or equal to two, and each of the first image obtaining device through the N-th image obtaining device is configured to receive image data corresponding to the image of the DUT captured by the image sensor;
   a first switch through a K-th switch, each of which is connected to a respective one of the first image obtaining device through the N-th image obtaining device, wherein K is a second natural number greater than or equal to two;
   a first image processing device through a M-th image processing device, each of which is connected to a respective one of the first switch through the K-th switch, wherein M is a third natural number greater than or equal to two, each of the first image processing device through the M-th image processing device is configured to:
      receive the image data that is output from one of the first image obtaining device through the N-th image obtaining device and is distributed by one of the first switch through the K-th switch, and
      generate a corresponding processed data by performing a processing operation on the image data; and
   a (M+1)th image processing device connected to one of the first switch through the K-th switch, wherein the (M+1)th image processing device is configured to:
      receive the image data, and
      generate additional processed data by performing an additional processing operation on the image data.

2. The inspection system of claim 1, wherein:
   the first image obtaining device receives first image data from the image sensor,
   the first switch is connected to the first image obtaining device,
   the first image processing device is connected to the first switch and receives the first image data that is distributed by the first switch,
   a second image processing device is connected to the first switch and receives the first image data that is distributed by the first switch,
   the first image processing device generates first processed data by performing a first processing operation on the first image data, and
   the second image processing device generates second processed data by performing a second processing operation on the first image data.

3. The inspection system of claim 2, wherein:
   the (M+1)th image processing device comprises an added image processing device,
   the added image processing device is configured to be electrically connectable to the first switch,
   wherein when the image processing device is connected to the first switch, the added image processing device receives the first image data and generates first additional processed data by performing a first additional processing operation on the first image data.

4. The inspection system of claim 3, wherein a structure of the image processing device is substantially the same as a structure of each of the first image processing device and the second image processing device.

5. The inspection system of claim 2, wherein the first image obtaining device comprises:
   a frame grabber configured to receive the first image data from the image sensor based on a first communication protocol;
   a network memory configured to output the first image data based on the first communication protocol; and
   a non-paged memory configured to control a data transmission between the frame grabber and the network memory in the first image obtaining device based on a second communication protocol that is different from the first communication protocol.

6. The inspection system of claim 5, wherein the network memory comprises a plurality of mapping memories.

7. The inspection system of claim 2, wherein the first image processing device comprises:
   a network memory configured to receive the first image data based on a first communication protocol;
   an at least one processing memory configured to perform the first processing operation on the first image data; and
   a non-paged memory configured to control a data transmission between the network memory and the at least one processing memory in the first image processing device based on a second communication protocol that is different from the first communication protocol.

8. The inspection system of claim 7, wherein the at least one processing memory comprises a graphic processing unit (GPU).

9. The inspection system of claim 7, wherein the network memory comprises an at least one mapping memory.

10. The inspection system of claim 2, wherein the first switch is located inside one of the first image processing device and the second image processing device.

11. The inspection system of claim 1, wherein a first number of the first image obtaining device through the N-th image obtaining device is different from a second number of the first image processing device through the M-th image processing device.

12. The inspection system of claim 11, wherein the second number of the first image processing device through the M-th image processing device is greater than the first number of the first image obtaining device through the N-th image obtaining device.

13. The inspection system of claim 11, wherein the first number of the first image obtaining device through the N-th image obtaining device and the second number of the first image processing device through the M-th image processing device are determined based on an amount of image data provided from the image sensor, at least one data transmission speed of the first image obtaining device through the N-th image obtaining device, and at least one processing speed of the first image processing device through the M-th image processing device.

14. The inspection system of claim 1, further comprising:
a determining device configured to determine whether the DUT has a defect based on an at least one of the processed data and the additional processed data.

15. The inspection system of claim 14, wherein the determining device is configured to determine whether the DUT has the defect based on a machine learning or a deep learning.

16. The inspection system of claim 1, wherein the first image obtaining device receives first image data from the image sensor, and a second image obtaining device receives second image data from the image sensor,
wherein the first image data and the second image data respectively correspond to a first portion of the DUT and a second portion of the DUT and the second portion is different from the first portion.

17. The inspection system of claim 1, wherein the first image obtaining device receives first image data from the image sensor, and a second image obtaining device receives second image data from the image sensor,
wherein the first image data and the second image data respectively correspond to a first DUT and a second DUT and the second DUT is different from the first DUT.

18. The inspection system of claim 1, wherein the image sensor comprises at least one of a charge-coupled device (CCD) image sensor and a complementary metal oxide semiconductor (CMOS) image sensor.

19. A method of inspecting a device under test (DUT), comprising:
capturing an image of the DUT;
receiving, by each of a first image obtaining device through a N-th image obtaining device, image data of the image of the DUT, where N is a first natural number greater than or equal to two;
distributing, by each of a first switch through K-th switch, the image data from one of the first image obtaining device through the N-th image obtaining device, where K is a second natural number greater than or equal to two, each of the first switch through the K-th switch connected to a respective one of the first image obtaining device through the N-th image obtaining device;
generating, by each of a first image processing device through a M-th image processing device, processed data by performing a processing operation on the image data, where M is a third natural number greater than or equal to two, each of the first image processing device through the M-th image processing device connected to a respective one of the first switch through the K-th switch; and
generating, by a (M+1)th image processing device, additional processed data by performing an additional processing operation on the image data when the additional processing operation for the image data is required, the (M+1)th image processing device configured to be electrically connectable to one of the first switch through the K-th switch.

20. A method of manufacturing a semiconductor device, comprising:
manufacturing a semiconductor substrate on which the semiconductor device is formed; and
inspecting the semiconductor substrate to determine whether the semiconductor substrate has a defect, the inspecting the semiconductor substrate comprising:
capturing an image of the semiconductor substrate;
receiving, by each of a first image obtaining device through a N-th image obtaining device, image data of the image of the semiconductor substrate, where N is a first natural number greater than or equal to two;
distributing, by each of a first switch through K-th switch, the image data from one of the first image obtaining device through the N-th image obtaining device, where K is a second natural number greater than or equal to two, each of the first switch through the K-th switch connected to a respective one of the first image obtaining device through the N-th image obtaining device;
generating, by each of a first image processing device through a M-th image processing device, processed data by performing a processing operation on the image data, where M is a third natural number greater than or equal to two, each of the first image processing device through the M-th image processing device connected to a respective one of the first switch through the K-th switch; and
generating, by a (M+1)th image processing device, additional processed data by performing an additional processing operation on the image data when the additional processing operation for the image data is required, the (M+1)th image processing device configured to be electrically connectable to one of the first switch through the K-th switch.

* * * * *